(12) United States Patent
Wolgast et al.

(10) Patent No.: US 10,346,671 B2
(45) Date of Patent: *Jul. 9, 2019

(54) FILMS FOR BIOLOGIC ANALYTE COLLECTION AND ANALYSIS AND METHODS OF PRODUCTION AND USE THEREOF

(71) Applicant: Diomics Corporation, San Diego, CA (US)

(72) Inventors: Beverly Lynn Wolgast, San Diego, CA (US); John F. Steel, La Jolla, CA (US); Thomas J. Kindt, Phoenix, AZ (US); Ryan B. Lamer, Spring Valley, CA (US)

(73) Assignee: Diomics Corporation, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/603,755

(22) Filed: Jan. 23, 2015

(65) Prior Publication Data

US 2016/0047720 A1 Feb. 18, 2016

Related U.S. Application Data

(60) Provisional application No. 62/037,919, filed on Aug. 15, 2014.

(51) Int. Cl.
| | |
|---|---|
| *A61B 5/1172* | (2016.01) |
| *G06K 9/00* | (2006.01) |
| *C12Q 1/6806* | (2018.01) |
| *A61B 5/145* | (2006.01) |

(52) U.S. Cl.
CPC ........ *G06K 9/00087* (2013.01); *A61B 5/1172* (2013.01); *A61B 5/14546* (2013.01); *C12Q 1/6806* (2013.01); *A61B 5/14507* (2013.01)

(58) Field of Classification Search
None
See application file for complete search history.

(56) References Cited

U.S. PATENT DOCUMENTS

| | | | |
|---|---|---|---|
| 4,455,206 A | 6/1984 | Funabashi et al. | |
| 5,129,402 A | 7/1992 | Koll et al. | |
| 5,484,882 A * | 1/1996 | Takada | C08G 63/08 528/272 |
| 5,545,681 A | 8/1996 | Honkonen | |
| 5,779,686 A | 7/1998 | Sato et al. | |
| 5,874,045 A | 2/1999 | Chisum | |
| 5,916,802 A | 6/1999 | Andreotti | |
| 5,935,799 A * | 8/1999 | Isbister | C12Q 1/10 422/82.05 |
| 5,977,203 A * | 11/1999 | Makuuchi | C08J 3/28 523/300 |
| 6,007,845 A * | 12/1999 | Domb | A61K 9/5153 424/451 |
| 6,103,255 A | 8/2000 | Levene et al. | |
| 6,184,011 B1 | 2/2001 | Siegel et al. | |
| 6,268,222 B1 | 7/2001 | Chandler et al. | |
| 6,447,991 B1 | 9/2002 | Daitch et al. | |
| 6,573,238 B2 * | 6/2003 | Shirley | A61K 9/0019 424/426 |
| 7,615,373 B2 | 11/2009 | Simpson et al. | |
| 7,655,070 B1 | 2/2010 | Dallas et al. | |
| 7,790,865 B1 | 9/2010 | Heath et al. | |
| 7,927,548 B2 | 4/2011 | Slowey et al. | |
| 7,978,074 B2 | 7/2011 | Nikitin et al. | |
| 8,049,623 B2 | 11/2011 | Morris et al. | |
| 8,586,345 B2 | 11/2013 | Simpson et al. | |
| 8,641,642 B2 | 2/2014 | Giddings et al. | |
| 8,685,747 B2 | 4/2014 | Zenhausern | |
| 8,696,595 B2 | 4/2014 | Sangha | |
| 8,759,075 B2 | 6/2014 | Morhet et al. | |
| 8,911,680 B2 | 12/2014 | Hanselle et al. | |
| 9,108,193 B2 | 8/2015 | Feiglin | |
| 9,200,321 B2 | 12/2015 | Caragine et al. | |
| 9,315,858 B2 | 4/2016 | Bearinger et al. | |
| 9,359,600 B2 | 6/2016 | Morhet et al. | |
| 9,988,664 B2 | 6/2018 | Ensor et al. | |
| 2001/0049148 A1 | 12/2001 | Wolk et al. | |
| 2002/0094531 A1 | 7/2002 | Zenhausern | |
| 2003/0129738 A1 | 7/2003 | Sorenson et al. | |
| 2003/0193118 A1 | 10/2003 | Bango et al. | |

(Continued)

FOREIGN PATENT DOCUMENTS

| | | |
|---|---|---|
| EP | 2249140 | 11/2010 |
| JP | 556061 | 2/1980 |
| WO | WO-9501165 A1 | 1/1995 |
| WO | 9803267 | 1/1998 |
| WO | 2004086979 A1 | 10/2004 |
| WO | WO-2005079531 A2 | 9/2005 |
| WO | 2006089297 | 8/2006 |
| WO | 2008157422 | 12/2008 |

(Continued)

OTHER PUBLICATIONS

Moon et al, J. Biomat. Sc. Pol. Ed., vol. 13, Abstract (2002) [retrieved on Dec. 8, 2016]. Retrieved from the Internet: <URL:http://www.tandfonline.com/doi/abs/10.1163/156856202760197438.*

(Continued)

*Primary Examiner* — Robert T. Crow
(74) *Attorney, Agent, or Firm* — Mintz, Levin, Cohn, Ferris, Glovsky & Popeo, P.C.

(57) ABSTRACT

Compositions, films, collection devices, apparatuses, kits and methods related to biologic analyte collection and analysis include thin films of modified polycaprolactone. Methods of production and use thereof are described herein. The films, compositions, collection devices, kits and methods can be used for collection of fingerprints for both image capture and nucleic acid extraction and analysis.

11 Claims, 4 Drawing Sheets

(56) References Cited

U.S. PATENT DOCUMENTS

| | | |
|---|---|---|
| 2003/0222012 A1 | 12/2003 | Lee et al. |
| 2004/0043443 A1 | 3/2004 | Lejeune |
| 2004/0132846 A1 | 7/2004 | Leventis et al. |
| 2004/0224362 A1 | 11/2004 | Gjerde et al. |
| 2005/0153346 A1 | 7/2005 | Schneider |
| 2005/0235848 A1 | 10/2005 | Butland |
| 2006/0199945 A1 | 9/2006 | Gjerde |
| 2006/0264133 A1 | 11/2006 | Krajewski et al. |
| 2007/0167900 A1 | 7/2007 | Kanjilal et al. |
| 2008/0070274 A1 | 3/2008 | Lee et al. |
| 2008/0299164 A1 | 12/2008 | Trollsas |
| 2009/0005722 A1* | 1/2009 | Jennings-Spring ............ A61F 13/00063 604/20 |
| 2009/0156962 A1 | 6/2009 | Yong |
| 2009/0162337 A1* | 6/2009 | Gross ............... A61K 9/5146 424/94.6 |
| 2009/0162407 A1 | 6/2009 | Biggs et al. |
| 2010/0003300 A1 | 1/2010 | Markland et al. |
| 2010/0113857 A1 | 5/2010 | Ramakrishna et al. |
| 2010/0137902 A1* | 6/2010 | Lee ................... A61L 24/001 606/213 |
| 2010/0226960 A1 | 9/2010 | Chudzik et al. |
| 2010/0239616 A1 | 9/2010 | Hafezi et al. |
| 2010/0274155 A1 | 10/2010 | Battrell et al. |
| 2010/0317051 A1 | 12/2010 | Hanselle et al. |
| 2011/0001609 A1 | 1/2011 | Oldham et al. |
| 2011/0004122 A1 | 1/2011 | Sangha |
| 2011/0008771 A1 | 1/2011 | Hanselle et al. |
| 2011/0027781 A1 | 2/2011 | Langlois et al. |
| 2011/0087133 A1 | 4/2011 | Ching et al. |
| 2011/0111503 A1 | 5/2011 | Siedel et al. |
| 2011/0245852 A1* | 10/2011 | Downes ............. A61L 27/18 606/152 |
| 2011/0250680 A1 | 10/2011 | Broyer et al. |
| 2011/0316268 A1 | 12/2011 | Aletto et al. |
| 2012/0034601 A1 | 2/2012 | Zenhausern et al. |
| 2012/0045752 A1 | 2/2012 | Ensor et al. |
| 2012/0122091 A1 | 5/2012 | Vom et al. |
| 2012/0128739 A1* | 5/2012 | Nygaard ............ A61L 27/34 424/400 |
| 2012/0129270 A1 | 5/2012 | Nallani et al. |
| 2012/0149021 A1 | 6/2012 | Yung et al. |
| 2012/0329081 A1 | 12/2012 | Bennion et al. |
| 2013/0267870 A1 | 10/2013 | Lonky |
| 2013/0345118 A1* | 12/2013 | Rolle ................. C07K 14/78 514/2.3 |
| 2014/0073988 A1 | 3/2014 | McSherry |
| 2014/0073989 A1 | 3/2014 | Vom et al. |
| 2014/0171828 A1 | 6/2014 | Blitzer et al. |
| 2016/0281079 A1 | 9/2016 | Morhet et al. |

FOREIGN PATENT DOCUMENTS

| | | |
|---|---|---|
| WO | WO-2008157422 A1 | 12/2008 |
| WO | 2009012808 | 1/2009 |
| WO | 2010123462 | 10/2010 |
| WO | 2011094745 | 8/2011 |
| WO | 2012024407 | 2/2012 |
| WO | 2014011536 | 4/2014 |

OTHER PUBLICATIONS

International Search Report dated Jun. 10, 2015 in PCT/2015/012627.
European Search Report dated Mar. 13, 2015 in Application No. EP 13 81 6496. (11 pages).
International Search Report and the Written Opinion of the ISA dated Dec. 20, 2013 in international Application No. PCT/US2013/049560. (17 pages).
Armani et al., "Microfabrication technology for polycaprolactone, a biodegradable polymer", J. Micromech. Microeng. PII: S0960-1317(00)08138-9, 10 (20000), 80-84.
B. Alp et al., "Crystallization Control of Polycaprolactone (PCL) with Inorganic and Organic Additives", 4 Pgs.
Naidoo et al., "An emulsion preparation for novel micro-porous polymeric hemi-shells", Science Direct, Material Letters 62, 2008, pp. 252-254.
Perego et al., "Functionalization of poly-L-lactic-co-e-caprolactone: effects of surface modification on endothelial cell proliferation and hemocompatibility", Improved endothelial adhesion for small diameter graft, J. Biomater. Sci. Polymer Edn, vol. 14, No. 10, 2003, pp. 1057-1075.
Pok et al., "In vitro characterization of polycaprolactone matrices generated in aqueous media", Acta Biomater, (Mar. 2010) 6(3): 1061-1068. doi: 10.1016/j.actbio.2009.08.00.
Spiess et al., "Trehalose is a potent PCR enhancer: Lowering of DNA metlting temperature and thermal stabilization of Taq Polymerase by the disaccharide trehalose", Clin Chem (Jul. 2004) 50(7): 1256-1259.
Thapa et al., "Polymers with nando-dimensional surface features enhance bladder smooth muscle cell adhesion", Enhancement of Bladder SMC Adhesion, Wiley Periodicals, Inc., 2003, pp. 1374-1383.
Woodruff et al., "The return of a forgotten polymer—Polycaprolactone in the 21st Century", Progress in Polymer Science, Apr. 2, 2010, pp. 1-40.
Zhang et al., "The encapuslation and intracellular delivery of trehalose using a thermally responsive nanocapsule", Nanotechnology (2009) 20 (275101): 1-14.
Tan et al. Effect of stiffness of polycaprolactone (PCL) membrane on cell proliferation Materials Science and Engineering C 27 2007) pp. 304-308 (Year: 2006).
Nair et al. Biodegradable polymers as biomaterials; Prog. Polym. Sci. 32 (2007) pp. 762-798 (Year: 2007).
International Search Report dated Oct. 19, 2015 in; PCT/US2015/041234.
Dzenitis et al., "The Autonomous Pathogen Detection System", The Microliow Cytometer, Mar. 16, 2009, pp. 263-286.
Madihally, S.V., et al. (2010). In vitro characterization of polycaprolactone matrices generated in aqueous media. Acta Materialia, 6(3), pp. 1061-1068.
"Polymer Cross-Linked Aerogels (X-Aerogels)," National Aeronautics and Space Administration, LEW-17685-1, Sep. 25, 2008, 2 pages, https://technology.grc.nasa.gov/support/images/GR-0013_LEW-17685(online).pdf.
Arote, Rohidas, et al. "A biodegradable poly (ester amine) based on polycaprolactone and polyethylenimine as a gene carrier." *Biomaterials* 28.4 (2007): 735-744.
Capadona, Lynn A., et al., "Flexible, low-density polymer cross-linked silica aerogels." Polymer 47.16 (2006): pp. 5754-5761.
Choong, Cleo SN, et al., "Co-culture of bone marrow fibroblasts and endothelial cells on modified polycaprolactone substrates for enhanced potentials in bone tissue engineering." Tissue engineering 12.9 (2006): 2521-2531.
Gadre, Mandar, et al., "Hybrid Nanomaterial Scaffolds for Specific Biomedical Applications." MRS Online Proceedings Library Archive vol. 1237 (2009), 6 pages.
Griffith, Linda G., and Melody A. Swartz, "Capturing complex 3D tissue physiology in vitro." Nature reviews Molecular cell biology 7.3 (2006): pp. 211-224.
Kanamori, Kazuyoshi, et al., "Elastic organic-inorganic hybrid aerogels and xerogels." Journal of Sol-Gel Science and Technology 48.1-2 (2008): pp. 172-181.
Leventis, Nicholas, et al., "Polymer nano-encapsulation of templated mesoporous silica monoliths with improved mechanical properties." Journal of Non-Crystalline Solids 354.2-9 (2008): 632-644.
Lowman, Anthony M., et al., "Structural and dynamic response of neutral and intelligent networks in biomedical environments." Advances in Chemical Engineering 29 (2004): pp. 75-130.
Murugan, Ramalingam, and Seeram Ramakrishna. "Design strategies of tissue engineering scaffolds with controlled fiber orientation." Tissue engineering 13.8 (2007): pp. 1845-1866.
Pierre, Alain C., and Gerard M. Pajonk. "Chemistry of aerogels and their applications." Chemical Reviews 102.11 (2002): 4243-4266.

(56) References Cited

OTHER PUBLICATIONS

Schulpis, Kleopatra H., et al. "Serum copper is decreased in premature newborns and increased in newborns with hemolytic jaundice." Clinical chemistry 50.7 (2004): 1253-1256.

Teo, Erin Yiling, et al. "Polycaprolactone-based fused deposition modeled mesh for delivery of antibacterial agents to infected wounds." *Biomaterials* 32.1 (2011): 279-287.

Voorhees, Jessica C., et al., "Enhanced elution of sperm from cotton swabs via enzymatic digestion for rape kit analysis." Journal of forensic sciences 51.3 (2006): 574-579.

Whatman® Brochure, "Innovative Solutions for Forensic DNA Collection, Archiving and Purification," 8 Pages, Apr. 2004, http://www.whatman.com/UserFiles/File/Brochures/Bioscience/Innovative%20Solutions%20for %20Forensics.pdf.

Zhang, Guohui, et al., "Isocyanate-crosslinked silica aerogel monoliths: preparation and characterization." Journal of Non-Crystalline Solids 350 (2004): 152-164.

Zhang, Shuguang, "Beyond the Petri dish." Nature biotechnology 22.2 (2004): pp. 151-152.

Zhang, Shuguang, et al., "Designer self-assembling peptide nanofiber scaffolds for 3D tissue cell cultures." Seminars in cancer biology. vol. 15. No. 5. Academic Press, 2005: pp. 413-420.

Zhu, Yabin, et al., "Surface modification of polycaprolactone with poly (methacrylic acid) and gelatin covalent immobilization for promoting its cytocompatibility." Biomaterials 23.24 (2002): 4889-4895.

\* cited by examiner

- Prepare 0.01 to 8.0% w/v polycaprolactone (PCL) in glacial acetic acid
- Incubate PCL solution at 60 to 65 C with stirring for 2 hrs
- Cool to room Temp (20 – 25 degree C)
- Pour into 250 ml Quorpak Glass Bottle
- Set up SprayBase Electrospray ; adjust time, voltage pressure.
- Use Spraybase or manually insert and spread solution onto defined surface.
- Place in lyophilizer with freezing *in situ;* lyophilize for 15 – 26 hrs
- Remove films on surface and place on benchtop
- Add 20 ml of 1.5 M NaOH for each film
- Let solution swirl gently for 1 hour at room temp.
- Pour off NaOH add equal vol of water repeat 3 times.
- Check pH if 8 or below continue if higher repeat washes.
- Remove from water and place on stainless steel mesh
- Dry at room temp 24 hrs
- QC to include water uptake, weight and thickness; test for sample uptake and DNA release
- Package, sterilize and label

FIG. 1

FILMS FOR BIOLOGIC ANALYTE COLLECTION AND ANALYSIS AND METHODS OF PRODUCTION AND USE THEREOF

CROSS-REFERENCE TO RELATED APPLICATIONS

This application claims the benefit of U.S. Provisional application 62/037,919, filed Aug. 15, 2014, hereby incorporated by reference in its entirety.

FIELD OF THE INVENTION

Films, compositions, collection devices, kits and methods related to biologic analyte and sample collection and analysis that include thin films of modified polycaprolactone (PCL) are described herein.

BACKGROUND

The collection of biologic samples is the first crucial step in a number of processes that utilize modern analytic techniques to identify sample source based on analyses of molecular components. These techniques may include genetic analyses to establish sample donor identity, for example.

A common use of DNA technology is the identification of individuals by the genetic profile of DNA present in the sample. Applications of such testing include forensic cases to match suspects with evidence, paternity testing to identify a child's father, missing persons identity, military "dog tag", convicted felon DNA data bases, victim identification in mass fatalities, and historic and genealogic investigations. These applications, for the most part, utilize genomic DNA which is found in most cells of the body (except, notably, in red blood cells) and which contains paternal and maternal derived genomic content. The potential applications have in common that all require a reference sample for comparison. The comparison samples may be relatives, samples from the tested individual or samples in an available database. Large databases of typing information for DNA samples are maintained by the FBI in the US, and by police agencies abroad, and, in many cases, newly acquired data are compared to these. Use of this information for forensics necessitates that all techniques used are efficient and reproducible and the processes by which the data are obtained must stand up as evidence in criminal court cases.

In some instances when sufficient nuclear DNA is not present, and with certain sample types (bone, hair, nails, charred remains), identification may rely on the analysis of mitochondrial DNA (mtDNA). Maternally derived, mtDNA, therefore yields different and more limited information than nuclear DNA. While mtDNA may establish sample genealogic origins and data on population migrations, only identity to mother and siblings rather than a general identity profile can be established.

A common element in all of the analyses of biologic analytes from acquired samples is the need for sufficient quantity of the desired substance to do necessary testing and the need for the analyte to be in a state that is amenable to the analyses that are performed to derive useful information. For the most commonly used DNA analyses, there must be sufficient sample (in most cases at least 1 ng of DNA) and the material must be reasonably intact so that pertinent sequences have not been degraded and further must not contain any materials that would interfere with test processes to be performed. Further requirements, such as protection from contamination, may accrue for samples that are collected in advance of the extraction and analysis processes and stored prior to use.

In order to address the growing demand for DNA analysis, including forensic DNA fingerprinting and medical diagnoses and analyses, there is a critical need for improvements in collection and analysis techniques. The medical and forensic DNA communities would therefore greatly benefit from a DNA technology platform suitable for DNA collection and analysis that is highly reliable and accurate.

SUMMARY

The synthetic polymer polycaprolactone (PCL) is modified and formulated as a thin film for collecting a sample that includes a biological analyte and provides for subsequent analysis of the biologic analyte(s). The thin films for biologic analyte collection as described herein lack materials that impede steps in preparation of a sample or in the analysis of a sample or biologic analyte(s) extracted therefrom (e.g., genotyping analyses for forensics applications, genetic analyses for medical diagnostics, etc.). The thin films can be easily manipulated for sample collection and analysis, for example, using forceps or with gloved hands. After drying the films are more easily handled. In some instances, such as for a tape, the film may be attached to a flexible backing.

Unless otherwise defined, all technical terms used herein have the same meaning as commonly understood by one of ordinary skill in the art to which this invention belongs.

By the term "biologic analyte" is meant any molecule, compound, protein, nucleic acid, small molecule, spore, or organism (a bacterium, bacterial spore, virus, mold, fungus, parasite) or any component of an organism. "Biologic analytes" include nucleic acids (e.g., methylated DNA), peptides, proteins, lipids, and carbohydrates, particularly those relevant to disease processes and/or forensic applications. A "biologic analyte" is typically present within a sample.

The term "sample" is used herein in its broadest sense. A sample that is collected using a film, composition, device, kit or method as described herein is any material to be analyzed. Examples include nucleic acids, cells, tissues, or bodily fluids such as blood, urine, semen, lymphatic fluid, cerebrospinal fluid, or amniotic fluid, or other biological samples, such as fingerprints, buccal swabs, mouthwashes, stool, tissue culture cells, tissues slices, biopsy aspiration, etc.

As used herein, "protein" and "polypeptide" are used synonymously to mean any peptide-linked chain of amino acids, regardless of length or post-translational modification, e.g., glycosylation or phosphorylation.

By the term "gene" is meant a nucleic acid molecule that codes for a particular protein, or in certain cases, a functional or structural RNA molecule.

As used herein the terms "nucleic acid" and "nucleic acid molecule" are intended to encompass single- and double-stranded DNA (deoxyribonucleic acid) and RNA (ribonucleic acid) (and forms thereof that can be partially single-stranded or partially double-stranded), as well as any and all forms of alternative nucleic acid containing modified bases, sugars, and backbones. Examples of DNA include eukaryotic or prokaryotic genomic DNA, oligonucleotides, mitochondrial DNA, cDNA, specific gene sequences, short tandem repeats (STRs), bacterial plasmids, bacteriophage DNA etc. The terms "nucleic acid" and "nucleic acid molecule" will be understood to include, but not be limited to DNA, RNA, cDNA, aptamers, peptide nucleic acids ("PNA"), 2'-5'

DNA (a synthetic material with a shortened backbone that has a base-spacing that matches the A conformation of DNA; 2'-5' DNA will not normally hybridize with DNA in the B form, but it will hybridize readily with RNA), and locked nucleic acids ("LNA"). Nucleic acid analogues include known analogues of natural nucleotides that have similar or improved binding, hybridization of base-pairing properties.

The terms "nucleic acid template" or "nucleic acid templates," as used herein, refer to a nucleic acid or nucleic acids that serve as starting material for the synthesis of an STR profile. Nucleic acid template(s) may be double stranded or single stranded. The templates can include DNA from one or more whole genomes of an individual, partial genomes of an individual, or previously amplified products from DNA of the individual and can include mixtures of whole and partial genomes from two or more individuals. The genomes to be analyzed may be derived from humans, from other mammalian species, or from mixtures.

The term "polymorphic site" as used herein refers to at least one nucleotide site in a DNA sequence that differs among certain individuals of a given species, such as humans.

The terms "locus" and "loci" (plural), as used herein, mean one or more specific positions within the whole or partial genomes of a given species, as defined herein.

The terms "STR locus" and "STR loci," as used herein, mean a nucleotide sequence consisting of a repeating pattern of two or more nucleotides at a given locus of a target nucleic acid. The repeating pattern can range in length from about 2 to about 10 base pairs (bp), and is typically in the non-coding intron region. The repeating pattern may contain intervening sequences that do not correspond to the repeat unit, or may contain more than one repeating pattern.

The terms "STR allele" or "allele," as used herein, refer to a form of an STR locus found in the genome of an individual. A given STR locus may be heterozygous, meaning that the two alleles (one inherited from each biological parent) are of different lengths and base pair composition, or may be homozygous, meaning that both alleles are of identical length (and usually but not always base pair composition). Rarely, an individual may have three or more alleles for a given STR locus. Occasionally, an individual's alleles at a given STR locus may differ from his or her parents due to one or more mutations.

As used herein, the term "film for collecting and analyzing a biologic analyte" means a thin layer of soluble and hydrophilic PCL having a thickness of less than about 0.6 millimeters (mm) e.g., between about 0.01 mm and 0.6 mm (e.g., 0.01, 0.02, 0.03, 0.04, 0.05, 0.06, 0.07, 0.08, 0.09, 0.1, 0.2, 0.3, 0.4, 0.5, 0.6 mm). Typically the PCL has been treated with a base (e.g., a base having a pH greater than 8 (e.g., NaOH, NaHCO$_3$, KOH, Na$_2$CO$_3$, and CA(OH)$_2$) and formulated as a film using the methods described below, and in some embodiments, also treated with a neutralizing agent for increasing hydrophilicity as described in U.S. Pat. No. 8,759,075. This patent is incorporated herein by reference in its entirety. Such a "film for collecting and analyzing a biologic analyte" is also referred to herein as a "thin film" and "a transparent or semi-transparent thin film" A film or thin film may have a backing applied or adhered to one side.

By the phrase "modified PCL" is meant any PCL that has been treated or modified such that the hydrophilicity of the PCL is increased and/or such that one or more surface features of the PCL have been modified (e.g., chemical and/or physical modifications). Examples of surface features include texture (e.g., roughness, smoothness), holes, dimples, channels, protrusions and other irregularities. Any suitable treatment methods, including chemical or physical treatments, for increasing hydrophilicity and/or modifying surface features of PCL can be used. For example, PCL can be subjected to (treated with) a base (e.g. having a pH above 8). Examples of bases include NaHCO$_3$ and NaOH.

As used herein, the phrase "soluble and hydrophilic PCL" means PCL that has been treated in some manner to make it absorb water and to become soluble in biologic analyte extraction reagents (e.g., DNA extraction solutions).

By the term "biologic analyte extraction reagent" is meant any reagent (e.g., solution) that can be used to extract or separate a biologic analyte from a sample. If the biologic analyte is a nucleic acid from a cell or organism, the extraction reagent is any reagent (e.g., nucleic acid extraction reagent or solution) that can be used to separate the nucleic acid (e.g., DNA, RNA, cDNA, mitochondrial DNA, genomic DNA) from the cell or organism. An extraction reagent used for nucleic acid extraction can be, for example, a solution containing one or more of: a detergent to disrupt cell and nuclear membranes, a proteolytic enzyme(s) to degrade proteins, an agent to inhibit nuclease activity, a buffering compound to maintain neutral pH, and chaotropic salts to facilitate disaggregation of molecular complexes. If protein assays are to be used for analyzing a biologic analyte, extraction solutions will not include proteolytic enzymes and may utilize organic solvents.

By the phrase "nucleic acid extraction reagent" is meant any reagent (e.g., solution) that can be used to obtain a nucleic acid (e.g., DNA) from biological materials such as cells, tissues, bodily fluids, microorganisms, etc. An extraction reagent can be, for example, a solution containing one or more of: a detergent to disrupt cell and nuclear membranes, a proteolytic enzyme(s) to degrade proteins, an agent to inhibit nuclease activity, a buffering compound to maintain neutral pH, and chaotropic salts to facilitate disaggregation of molecular complexes.

As used herein, the term "carrier" refers to any structure or implement to which modified PCL is coupled, adhered, or disposed on or within. A carrier as described herein assists man or machine in exposing modified PCL to a biologic analyte, and subsequent processing, e.g., hand held or "machine-held." Examples of carriers include rigid and semi-rigid materials, such as wood, plastic, glass, rubber, and polymers.

As used herein, the term "copolymerized" refers to using two or more monomeric units to form a polymer with inclusion of both in some random (e.g., AABABB-BAABAAABBBBA) or defined order (such as, e.g., AAABAAABAAAB or ABABABAB or ABAABAABAABAABAABA). For example, when referring to PCL that is copolymerized with at least one agent such as, e.g., L-lactic acid, the copolymer formed is a poly caprolactide called poly-L-lactic-co-ε-caprolactone.

The phrase "under conditions that result in soluble and hydrophilic PCL" encompasses any suitable methods and steps for treating PCL, a solubilized PCL solution, or a solubilized PCL solution-coated carrier or mold that contribute to an increase of hydrophilicity and/or solubility during preparation of a thin film as described herein. Conditions may include, for example, treatment with a base prior to neutralization, one or more drying steps, one or more washing steps, etc.

By the term "neutralizing agent" is meant any reagent (e.g., a solution, liquid, etc.) that when contacted with PCL, for example, brings the pH of the PCL to a neutral pH. Nonlimiting examples of neutralizing agents include water and acidic solutions.

The terms "patient," "subject" and "individual" are used interchangeably herein, and mean a mammalian (e.g., human, rodent, non-human primates, canine, bovine, ovine, equine, feline, etc.) subject to obtain a biologic sample from.

The phrases "isolated" or "biologically pure" refer to material which is substantially or essentially free from components which normally accompany it as found in its native state.

The term "sample" is used herein in its broadest sense. A sample may include a bodily fluid, a soluble fraction of a cell preparation or media in which cells were grown, genomic DNA, RNA or cDNA, a cell, a tissue, skin, hair, saliva, serum, blood, urine, buccal cells, plasma, and the like.

Materials through which light passes without being scattered are transparent; those materials through which no light passes are opaque. As used herein, the term "semi-transparent" is meant to describe an in-between state with partial passage of light, usually a cloudy or smoky appearing medium.

As used herein, the phrase "surface of forensic interest" means any surface area of interest to law enforcement personnel because of a crime, or suspected crime in that area. For example, a weapon or any object handled by a potential perpetrator of crime may include a surface of forensic interest and used to obtain fingerprints or DNA to identify the person of interest. A gun trigger or recovered stolen object may include a surface to be scanned for evidence.

The phrase "a trace sample's donor" as used herein means an individual (the donor) who has left evidence of having been in an area; if the evidentiary sample is very small it is considered a trace sample. A partial human fingerprint, for example, can be considered a trace sample, and the human who left the fingerprint or to whom the fingerprint belongs is the donor of the fingerprint or trace sample.

Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

Accordingly, described herein is a transparent or semi-transparent thin film that is produced by electrospray and that includes PCL. At least a portion of the film solubilizes when exposed to at least one reagent for extraction of biological analytes. The films described herein can be used for collecting and analyzing a biologic analyte (e.g., a nucleic acid) and/or a biological sample (e.g., a fingerprint). In a typical embodiment, the film has a thickness in the range of about 0.01 mm to about 0.6 mm. The PCL can be copolymerized with at least one of the following agents: an acrylamide and a polyester other than PCL. The at least one agent can be one or more of: polylactide, polyglycolide, polydioxanone, acrylamide, poly N-isopropylacrylamide, and polyurethane. The film can be sterilized such that it is free of nucleic acids. In some embodiments, a backing has been applied or adhered to one side of the film (e.g., for use or inclusion of the film in a dispenser apparatus). In some embodiments, the transparent or semi-transparent thin film is packaged within packaging, and the packaging includes an identifying label or a radio-frequency identification (RFID) tag.

A transparent or semi-transparent thin film produced by the following steps is also described herein: solubilizing PCL in a solvent resulting in a solution; applying the solution to a mold using an electrospray instrument; freezing the solution; lyophilizing the electrosprayed solution to remove solvent resulting in a film; subjecting the film to treatment with a base having a pH greater than 8 and a neutralizing agent under conditions that result in soluble and hydrophilic PCL; and drying the film. This method of producing the transparent or semi-transparent thin film can also include sterilizing the transparent or semi-transparent thin film such that it is free of nucleic acids. The method can further include attaching the transparent or semi-transparent thin film to a carrier. In some embodiments, the method further includes packaging the transparent or semi-transparent thin film (e.g., after the transparent or semi-transparent thin film has been sterilized and optionally, attached to a carrier).

Also described herein is a dispenser apparatus that includes an elongate length of a transparent or semi-transparent thin film as described herein formed into a roll wound around a spindle. The dispenser apparatus can also include a cutting tool for cutting the transparent or semi-transparent thin film.

Further described herein is a method of collecting and analyzing a biologic analyte. The method includes the steps of: contacting a transparent or semi-transparent thin film as described herein with a sample including a biologic analyte such that the sample is reversibly adhered to the PCL; contacting the transparent or semi-transparent thin film and the sample with at least one biologic analyte extraction reagent under conditions such that the PCL is solubilized and the sample is separated from the transparent or semi-transparent thin film; collecting the separated sample; and separating the biologic analyte from the sample. In one embodiment of the method, the biologic analyte is at least one nucleic acid and separating the biologic analyte from the sample includes subjecting the separated sample including the biologic analyte to a nucleic acid extraction reagent and extracting the at least one nucleic acid from the separated sample. The at least one nucleic acid can be, for example, eukaryotic or prokaryotic genomic DNA, an oligonucleotide, mitochondrial DNA, cDNA, a short tandem repeat (STR), a bacterial plasmid, a bacteriophage DNA, etc. The sample can be, for example, cells, tissue, blood, urine, semen, lymphatic fluid, cerebrospinal fluid, amniotic fluid, a fingerprint, a buccal swab, mouthwash, stool, tissue culture cells, tissues slices, a tumor biopsy, a biopsy aspirate, etc. In one embodiment, the sample can be obtained from, for example, cells, tissue, blood, urine, semen, lymphatic fluid, cerebrospinal fluid, amniotic fluid, a fingerprint, a buccal swab, mouthwash, stool, tissue culture cells, tissues slices, a tumor biopsy, a biopsy aspirate, etc. The method can further include the step of analyzing the biologic analyte, and analyzing the biologic analyte can include at least one of: nucleic acid sequencing, forensic analysis, comparing the sample to those contained in the Combined DNA Index System (CODIS), protein assay, chemical analysis, immunoassay, mass spectrometry, microarray analysis, and detection of radioactive material. In one example, the sample is obtained from a human subject, the biologic analyte is at least one nucleic acid, and analyzing the biological analyte includes nucleic acid sequencing. Analyzing the biologic analyte can result in a DNA profile and determination of the human subject's identify. The method can further include comparing the DNA profile to a reference sample. In some embodiments of the method, in addition to analyzing the biologic analyte, the sample (e.g., a fingerprint) is also analyzed. For example, if the biologic analyte (e.g., nucleic acid) is obtained from a fingerprint (i.e., the sample), the fingerprint can also be analyzed. In some embodiments, analysis of the biologic analyte (e.g., DNA) and the sample (e.g., fingerprint) can be done simultaneously.

Still further described herein is a method of genotyping a sample that includes a nucleic acid. The method includes: collecting or providing a sample that includes a nucleic acid using a transparent or semi-transparent thin film as described herein, wherein the sample is reversibly adhered to the film; contacting the transparent or semi-transparent thin film and the sample with at least one nucleic acid extraction reagent under conditions such that the PCL is solubilized and the sample is separated from the transparent or semi-transparent thin film; separating the nucleic acid from the sample; and analyzing the nucleic acid for a plurality of genetic markers (e.g., alleles) at a plurality of STR loci (e.g., one or more CODIS STR loci) and generating a DNA profile that may be compared to at least one other DNA profile in at least one DNA database (e.g., the National DNA Index System). The DNA profile may be assigned a Specimen Identification Number. In one embodiment, the sample is a human buccal sample or blood sample, and comparing the DNA profile to the at least one other DNA profile in at least one DNA database includes use of CODIS software. In another embodiment, the sample is obtained from a fingerprint directly applied to the transparent or semi-transparent thin film or from a fingerprint from at least one surfaces of forensic interest (e.g., a crime scene, contraband materials, etc.). In the method, the sample can be a fingerprint, for example.

Also described herein is a kit for identifying the donor of a sample such as a trace sample (e.g., a trace sample's donor). The kit includes: at least one transparent or semi-transparent thin film as described herein; at least one biologic analyte extraction reagent; packaging; and instructions for use. In one embodiment of the kit, the transparent or semi-transparent film is used for collection of DNA from latent fingerprints and to obtain images of the latent fingerprints. In this embodiment, the at least one biologic analyte extraction reagent is unaffected by fingerprint visualization materials. In such an embodiment, the kit can also include one or more reagents (e.g., fingerprint visualization materials) and/or devices (e.g., inkpad) for analyzing the fingerprint. The kit can include a plurality of the transparent or semi-transparent films, and each transparent or semi-transparent thin film can be individually packaged. Each package can include an identifying label, and an RFID tag or a bar code.

Yet further described herein is a fingerprinting kit that includes a housing having side walls coupled to a solid support and a lid, and at least one panel consisting of a transparent or semi-transparent thin film as described herein disposed in the interior of the housing.

Other features will become more apparent to persons having ordinary skill in the art to which the package pertains and from the following description and claims. Although films, compositions, apparatuses, devices (thin film collection devices), kits, and methods similar or equivalent to those described herein can be used in the practice or testing of the present invention, suitable films, compositions, apparatuses, devices (thin film collection devices), kits, and methods are described below. All publications, patent applications, and patents mentioned herein are incorporated by reference in their entirety. In the case of conflict, the present specification, including definitions, will control. The particular embodiments discussed below are illustrative only and not intended to be limiting.

BRIEF DESCRIPTION OF THE DRAWINGS

The above and other aspects, features and advantages of the present embodiments will be more apparent from the following more particular description thereof, presented in conjunction with the following figures.

FIG. 1 is a flow chart of one embodiment of a method of production of a thin film as described herein.

DETAILED DESCRIPTION

Figure 2:
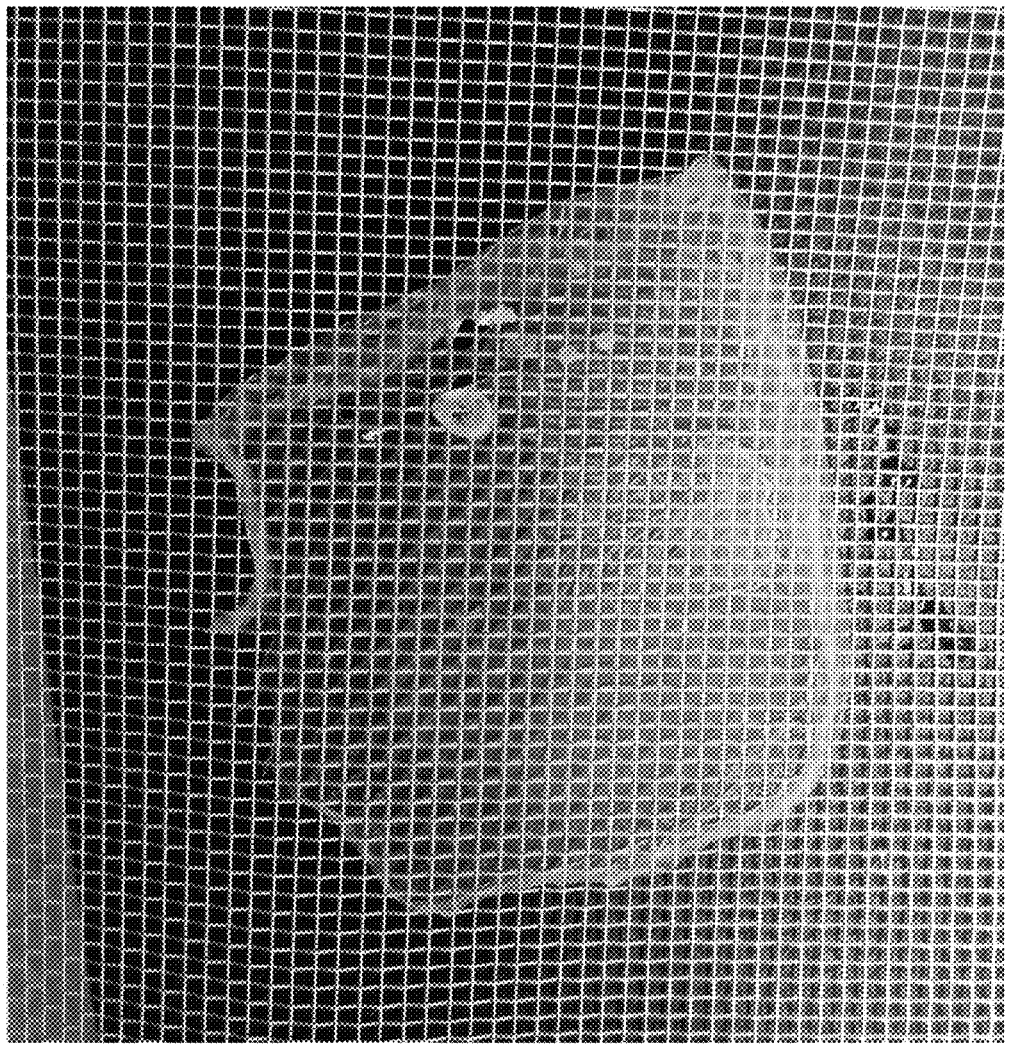
FIG. 2 is a photograph of a thin film as described herein adhered to a mesh screen. This was prepared using 2% PCL as described in Example 2 below.

The following description is not to be taken in a limiting sense, but is made merely for the purpose of describing the general principles of exemplary embodiments. The scope of the embodiments should be determined with reference to the claims. Such thin films, thin film collection devices, apparatuses, kits and methods can be useful in medical applications (e.g., diagnostics) and forensics (e.g., DNA profiling, DNA fingerprinting). The present embodiments provide materials that absorb samples (e.g., biological samples) efficiently, yet are soluble in extraction reagents (e.g., nucleic acid extraction buffers). This results in high yields of, for example, DNA suited to DNA profiling using, for example, short tandem repeats (STRs). The apparatuses, kits and devices described herein can be paired with software that can store a variety of detailed information concerning the nature of the sample(s) taken. The thin films, thin film collection devices, kits and apparatuses as described herein are able to be manufactured in a scalable fashion (e.g., large-scale) to provide consistent and reliable collection materials.

Soluble and Hydrophilic PCL

PCL is a biodegradable polyester that is insoluble in water and retains its hydrophobic character when mixed with other resins and plastics. PCL has a low melting temperature (60° C.) and is easily malleable making it ideal for certain molding applications. PCL has low hydrophilicity (i.e., a low affinity for water; not easily absorbing or dissolving in water). Thus, the thin films described herein include PCL that has been modified or treated to be soluble and hydrophilic. PCL can be modified to be soluble and hydrophilic as described in U.S. Pat. No. 8,759,075, incorporated herein by reference. Methods of formulating soluble and hydrophilic PCL into thin films are described below.

Thin films comprising soluble, hydrophilic PCL efficiently adsorb samples of various types such as bodily fluids, cells shed from fingerprints, and the like, with no or limited adverse affects to targeted samples. Such materials release samples with high efficiency using, for example, commercially available DNA extraction kits. PCL as presented herein is modified to improve its hydrophilicity. Such PCL modification enhances absorbency, sterility and freedom from contaminating DNA. PCL can be modified using any suitable chemical or physical methods. One or more surface features of PCL can be modified (or added) to increase hydrophilicity.

PCL is a homopolymer made by a ring-opening polymerization of epsilon caprolactone. Similar polymers are polylactide, polyglycolide or polydioxanone. PCL may be copolymerized with other esters such as polylactide to alter properties. In addition to polylactide, PCL may be copolymerized with other lactone-containing polymers such as poly-glycolide, poly (3 to 10-membered) lactone ring-containing compounds, etc. Generally, high molecular weight (MW) biodegradable lactone co-polymers are used, but poly ethylene glycol and poly vinyl styrene can also be used. In a typical embodiment, a molecular weight range of PCL is 5 K to 300 K. For example, an 80 K MW PCL polymer can be used.

Polymers of acrylamide may also be used, such as poly N-isopropylacrylamide. The addition of derivative groups to the PCL polymerization reaction may be used to change properties of the PCL. For example, the carbohydrate trehalose can be used to enhance DNA stability. Soluble, hydrophilic PCL can be impregnated with a bacteriostatic or fungicidal substance to inhibit bacterial growth for samples in storage. Other possible modifications include inhibitors of enzymes (such as DNAse or other nucleolytic enzymes) that can degrade the sample. In other approaches, soluble, hydrophilic PCL can be modified by coupling a protein to PCL, such as an antibody.

An important factor in obtaining a high yield of DNA, for example, from biological samples is the ability of the collection material (i.e., a thin film as described herein) to release the material and the extracted DNA into extraction reagent solutions. The fact that the hydrophilic, soluble PCL thin films described herein dissolve (are solubilized) in most of the commonly used extraction solutions facilitates high yields of DNA. Success of DNA typing is related to the amount of target material recovered from an evidentiary item. Generally, the more DNA that is recovered, the better the chance is of obtaining a typing result that will be robust and reliable. A favored method of collecting stain materials is by swabbing. Successful recovery of DNA relies on two qualities of a swab, i.e., absorption and adsorption. The two features impact the ability to collect materials from a stain or surface and then release the cells/DNA during the extraction process. Swabs that are proficient at collecting materials often are less efficient at releasing DNA from the swab matrix, and vice versa. Indeed, it is well-known that recovery of DNA from a swab is inefficient. In fact, van Oorschot et al. (van Oorschot R A, Ballantyne K N, Mitchell R J. Forensic trace DNA: A review. Investig Genet. 2010 12; 1(1):14,2223-1-14) suggested that a significant proportion of DNA (20-76%) that is collected by a cotton cloth/swab is lost during the extraction phase which may be attributed to the collecting agent (swab, cloth, etc.) and the condition of the sample.

Recovery of DNA from a number of commercially-available swabs reveals that this is not an efficient process. By contrast, a swab (collection device) made of PCL modified and prepared according to the methods of U.S. Pat. No. 8,759,075, referred to herein as the X-Swab™ (Diomics Corporation, Carlsbad, Calif.) is a unique bio-specimen collection material with highly absorptive properties and can be disrupted and at least partially dissolved during certain extraction conditions. Therefore, more DNA may be collected from a substrate and be released from the swab matrix than other swabs. Initial efforts the DNA yield from the X-Swab™ was compared in head-to-head tests against cotton swabs (Puritan) and showed superior results for both blood and saliva samples. Typical results indicated that approximately 10% of the DNA present in an acquired 1 ul blood samples would be recovered using cotton while the X-Swab™ consistently yielded over 60% and sometimes as high as 85%.

In recent tests, the ability to recover DNA from X-Swab™ material, and success in STR typing were compared with the Copan 4N6FLOQSwab™ (Brescia, Italy), a device which utilizes a proprietary flocked-swab technology to maximize DNA collection and elution efficiency. Both types of swabs were impregnated with known amounts of DNA and body fluids and allowed to air dry. In addition, blood was placed onto glass slides, allowed to dry and collected using both types of swabs. DNA recovery was assessed by DNA quantitation and by STR typing. Results suggested that X-Swab™ material yielded greater DNA recovery, particularly of low quantity samples (defined as diluted neat samples), compared with the 4N6FLOQSwab™. Results also indicated that X-Swab™ material itself enhances yield of PCR products. In a comparison of the collectors when used to pick up dried blood samples of 1 and $\frac{1}{10}$ ul in volume from glass slides, the results revealed that even when samples as small as $\frac{1}{10}$ ul of blood were acquired, sufficient DNA (>1 ng) to carry out analysis of STR for sample identification were obtained in 70% of the cases. Further and more detailed studies of samples acquired using the X-Swab™ asked whether the samples obtained were of good enough quality for more complete analyses. Amplified STR loci prepared using the methodology described in U.S. Pat. No. 8,759,075 indicated that the material extracted from the X-Swab™ was of good quality and usable to provide a complete CODIS profile for subject identity. In addition to the high yields of quality DNA, the X-Swab™ used in the study also showed some enhancement of DNA yields obtained in the PCR processes that follow sample extraction. STR typing results suggested that DNA extracted from X-Swab™ material tended to yield increased peak heights compared with DNA from the 4N6FLOQSwab™. When DNA extracted from both swabs was normalized to 1 ng and then typed for STRs with Identifiler Plus (28 cycles), X-Swab™ material consistently yielded higher RFUs at all loci, some substantially higher, when compared with DNA from the 4N6FLOQSwab™. To test whether the solubilized polymer from the X-Swab™ material may be affecting PCR yield, clean X-Swab™ material (i.e., no DNA) was subjected to the DNA extraction protocol. DNA (500 pg) from liquid whole blood and either 9 .mu·L of sterile water or X-Swab™ extract were placed in amplification reactions (29 cycles). The PCRs with X-Swab™ extract yielded higher RFU values at all loci compared with those with water and no differences were observed in the average PHR. These results are presented in Marshall P L et al., "Evaluation of a Novel Material, Diomics X-Swab™, for Collection of DNA," Forensics Science International: Genetics published online 26 Jun. 2014.

Nucleic Acid Extraction Methodology

Several of the methods described herein involve extraction of a nucleic acid from a sample. These methods can be used in forensics as well as medical applications. Nucleic acid extraction can be performed using any suitable methodology. With regard to forensics, for example, samples taken from crime scenes and those used as references to identify these acquired samples must go through a several step process to yield data suited for comparison and identification. The first step is sample collection that may involve swabbing stains from a crime scene or taking a blood or buccal cell sample from a suspect for comparison. (If no suspect has been identified, the data obtained may be compared to samples in databases maintained by the FBI and other law enforcement agencies.) The sample is then stored in a manner to prevent any contamination by cells from other individuals and is kept dry to avoid growth of any biologic agents, such as bacteria or fungi, that may degrade the sample. The next step is extraction of DNA and quantification to determine if there is sufficient for the subsequent analyses.

Extraction and purification of nucleic acids, proteins or other biologic analytes from samples using conventional techniques are significant challenges. Since molecular genetics, genomics and informatics will be central to future diagnostics, the methods described herein involving DNA collection (recovery) are suited for subsequent analyses by standard genetic typing used for forensics samples. However, the rapid progress in obtaining whole genome sequences by newly developed techniques and instrumentation makes it mandatory to retrieve sufficient quantities and to maintain the integrity of nucleic acids for sequencing. Any techniques used must optimize the chances of characterizing the material to the highest possible level without costly retesting.

Extraction is usually necessary as a sample-processing step between collection and analysis. A wide variety of options exist for extracting nucleic acids for analysis. Ideally, extraction protocols should be simple and inexpensive to perform. A collection medium should be compatible with a number of extraction procedures. Standard DNA extraction procedures may entail 1) organic solvent, 2) salting out methods, 3) cation exchange resins, such as Chelex-100; or 4) silica-based methods (2,6-11) Many laboratories are moving away from organic phenol-chloroform extraction because of the toxic reagents involved, although it still is one of the best extraction procedures for purifying nucleic acids. The preferred non-organic methods are silica-based methods, such as QIAquick® columns (Qiagen, Valencia, Calif.), which utilize silica membrane spin columns to bind and elute DNA. The bind-capture-elute methods have proven to be successful for purifying DNA for the PCR from samples containing inhibitors.

Methods involving conventional molecular biology techniques are described herein. Such techniques are generally known in the art and are described in detail in methodology treatises such as Molecular Cloning: A Laboratory Manual, 3rd ed., vol. 1-3, ed. Sambrook et al., Cold Spring Harbor Laboratory Press, Cold Spring Harbor, N. Y., 2001; and Current Protocols in Molecular Biology, ed. Ausubel et al., Greene Publishing and Wiley-Interscience, New York, 1992 (with periodic updates).

Samples and Biologic Analytes to be Collected and Analyzed

Samples include any biologic analyte (e.g., nucleic acid)-containing material (e.g., a biologic material). Samples may be those obtained directly from a subject (e.g., a human subject) or those indirectly obtained from a subject (e.g., samples that have been processed in some way prior to obtainment from the subject, samples left at a crime scene, etc.). Types of useful samples include eukaryotic samples, plant samples, animal samples, vertebrate samples, fish samples, mammalian samples, human samples, non-human samples, bacterial samples, microbial samples, viral samples, biological samples, serum samples, plasma samples, blood samples, urine samples, semen samples, lymphatic fluid samples, cerebrospinal fluid samples, amniotic fluid samples, biopsy samples, needle aspiration biopsy samples, cancer samples, tumor samples, tissue samples, cell samples, cell lysate samples, crude cell lysate samples, tissue lysate samples, tissue culture cell samples, buccal swab samples, mouthwash samples, stool samples, autopsy samples, infection samples, nosocomial infection samples, production samples, drug preparation samples, biological molecule production samples, protein preparation samples, lipid preparation samples, carbohydrate preparation samples, fingerprints, etc. Types of forensics samples include blood, dried blood, bloodstains, buccal swabs, fingerprints, touch samples (e.g., epithelial cells left on the lip of a drinking glass, the inner rim of a baseball cap, or cigarette butts), nucleated cells obtained by various means and material taken in forensic investigations that may include cells shed in fingerprints, laser-dissected cells, chewing gum, gastric contents, saliva, nail scrapings, soil, sexual assault samples including sperm and vaginal epithelial cells, hair, bone, skin, any bodily fluid, and solid tissue.

A typical biologic analyte is a nucleic acid. Nucleic acids include, for example, human nucleic acids, bacterial nucleic acids, or viral nucleic acids. A nucleic acid (or nucleic acid sample) can be, for example, from one or more cells, tissues, or bodily fluids such as blood, urine, semen, lymphatic fluid, cerebrospinal fluid, or amniotic fluid, or other biological samples, such as fingerprints, buccal swabs, mouthwashes, stool, tissue culture cells, tissues slices, biopsy aspiration, etc. Nucleic acids can be derived from any source including, but not limited to, eukaryotes, plants, animals, vertebrates, fish, mammals, humans, non-humans, bacteria, microbes, viruses, biological sources, serum, plasma, blood, urine, semen, lymphatic fluid, cerebrospinal fluid, amniotic fluid, biopsies, needle aspiration biopsies, cancers, tumors, tissues, cells, cell lysates, crude cell lysates, tissue lysates, tissue culture cells, buccal swabs, mouthwashes, stool, mummified tissue, forensic sources, autopsies, archeological sources, infections, nosocomial infections, production sources, drug preparations, biological molecule productions, protein preparations, lipid preparations, carbohydrate preparations, inanimate objects, air, soil, sap, metal, fossils, etc. A sample or nucleic acid sample may also contain mixtures of material from one source or different sources. For example, nucleic acids of an infecting bacterium or virus can be present along with human nucleic acids when nucleic acids from such infected cells or tissues are collected and analyzing using the disclosed methods.

Because the goal of the thin films and thin film collection devices in some embodiments is to obtain a useable genetic profile of the individual or subject from whom the sample was directly or indirectly obtained, the quality of DNA obtained and its suitability for subsequent testing is important. The thin films and thin film collection devices described herein acquire sufficient sample and yield sufficient DNA to allow standard analyses to be performed.

Films for Collecting and Analyzing a Biologic Analyte ("Thin Films")

A film for collecting and analyzing a biologic analyte includes soluble and hydrophilic PCL and has a thickness of less than about 0.6 mm (e.g., 0.01, 0.02, 0.03 mm, 0.05 mm, 0.07 mm, 0.09 mm, 0.1 mm, 0.2 mm, 0.3 mm, 0.4 mm, 0.5 mm, 0.6 mm) and is transparent or semi-transparent. At least a portion of the PCL solubilizes when exposed to a biologic analyte extraction reagent. In such a film (a thin film), PCL can be copolymerized with one or both of an acrylamide and a polyester other than PCL (e.g., one or more of polylactide, polyglycolide, polydioxanone, acrylamide, poly N-isopropylacrylamide, and polyurethane). Before use, a thin film typically has been sterilized. The thin film can be sterilized prior to packaging, or sterilized after it is packaged. In an embodiment in which the film is packaged, the packaging can include an identifying label and/or a radio-frequency identification (RFID) tag.

Thin films comprising soluble, hydrophilic PCL can take the form of various shapes and configurations, including any two-dimensional shapes and configurations. Variables affecting shape can include consideration of the sample origin to be collected, manufacturing efficiency, material economy, storage, clearance within a container, and the like and combinations thereof

Dispensers of Thin Films

Ease of operator use can be aided by the assembly of a thin film into a container such as a plastic container. Although such a container will generally be plastic, any suitable material(s) (e.g., glass) can be used. The entire assembly can be sterilized and rendered nucleic acid (e.g., DNA, RNA)-free by any suitable means or process (e.g., exposure to ultraviolet or gamma radiation at an intensity and time that destroys any nucleic acids on the collector). The sterilization process also preferably kills any microorganisms present. The plastic container keeps the thin film sterile and DNA-free prior to use. In one embodiment, an apparatus includes a roll of thin film as described herein. Such apparatuses act as a dispenser of the thin film. An apparatus may be formed, for example, as a conventional tape dispenser. Conventional tape dispensers are well known in the art, and are described, for example, in U.S. Pat. Nos. 8,720,521, 8,474,504, 2,295,477, D701,901, etc., all of which are incorporated herein by reference.

In one example of such an embodiment, a dispenser apparatus includes an elongate length of a thin film as described herein that is formed into a roll wound around a spindle. Such an apparatus can also include a cutting tool for cutting the elongate length of the film, e.g., cutting portions of the thin film.

Methods of Collecting and Analyzing a Biologic Analyte

A method of collecting and analyzing a biologic analyte includes the steps of: contacting a thin film as described herein with a sample (e.g., cells, tissue, blood, urine, semen, lymphatic fluid, cerebrospinal fluid, amniotic fluid, fingerprint, buccal swab, mouthwash, stool, tissue culture cells, tissues slices, tumor biopsy, biopsy aspirate, etc.) that includes a biologic analyte such that the sample is reversibly adhered to the PCL; contacting the film and the sample with at least one biologic analyte extraction reagent under conditions such that the PCL is solubilized and the sample is separated from the film; collecting the separated sample; and separating the biologic analyte from the sample. In one embodiment, the biologic analyte is at least one nucleic acid (e.g., eukaryotic or prokaryotic genomic DNA, oligonucleotide, mitochondrial DNA, cDNA, STR, bacterial plasmid, and bacteriophage DNA) and separating the biologic analyte from the sample includes subjecting the separated sample that includes the biologic analyte to a nucleic acid extraction reagent and extracting the at least one nucleic acid from the separated sample. The method can further include the step of analyzing the biologic analyte. For example, the sample can be obtained from a human subject, the biologic analyte can be at least one nucleic acid, and analyzing the biologic analyte can include nucleic acid sequencing. In this example, analyzing the biologic analyte can result in a DNA profile and determination of the human subject's identity. Analyzing the biologic analyte can further include comparing the DNA profile to a reference sample. Analyzing the biologic analyte can include any appropriate methodology, including, for example, nucleic acid sequencing, forensic analysis, Combined DNA Index System (CODIS), protein assay, chemical analysis, immunoassay, mass spectrometry, microarray analysis, and detection of radioactive material.

In the films, compositions, apparatuses, methods, devices and kits described herein, sufficient nucleic acid (e.g., DNA) is typically extracted from a sample such that amplification of the extracted nucleic acid is not required prior to specific analysis. However, in an embodiment in which amplification is useful or required, any suitable method for amplifying a nucleic acid may be used. Methods of polymerase chain reaction (PCR) amplification are well known in the art.

Methods of Genotyping a Sample

A typical method of genotyping a sample that includes a nucleic acid includes the following steps: collecting or providing the sample using a film as described herein, wherein the sample is reversibly adhered to the film; contacting the film and the sample with at least one nucleic acid extraction reagent under conditions such that the PCL is solubilized and the sample is separated from the film; separating the nucleic acid from the sample; and analyzing the nucleic acid for a plurality of genetic markers at a plurality of STR loci and generating a DNA profile. The sample can be, for example, a human buccal sample or blood sample. Alternatively, the sample can be obtained from a fingerprint. The method can further include assigning a Specimen Identification Number to the DNA profile, and/or comparing the DNA profile to at least one other DNA profile in at least one DNA database. Exemplary embodiments of this method are described below.

The thin films and thin film collection devices described herein are made from materials that do not react with a collected sample or specimen in unexpected ways, unless configured to do so, and preferably are not effected by exposure to altered levels of various environmental conditions, such as elevated ultraviolet (UV) light. The thin films and thin film collection devices, apparatuses, methods and kits described herein provide nucleic acids and nucleic acid samples that when analyzed, provide data suitable for forensic interpretation. Forensic interpretation guidelines are known, and are described, for example, in Scientific Working Group on DNA Analysis Methods, Short Tandem Repeat (STR) Interpretation Guidelines. Forensic Science Communications, 2000, 2(3). In a typical embodiment, sample/specimen profile analysis data is reportable in a format usable with the Combined DNA Index System (CODIS), for example. CODIS provides a searchable database of DNA profiles to assist in the identification of suspects in crimes.

A commonly used method for identification of DNA samples for forensic purposes relies upon typing of STRs (short tandem repeats) at 13 polymorphic autosomal loci coupled with analysis of the amelogenin gene to determine gender of the sample donor, i.e., the system of CODIS. CODIS is a software platform that blends forensic science and computer technology. CODIS has multiple levels where DNA profiles can be stored and searched: the local level (for city and county DNA laboratories), state level and national level. Data stored at the national level is kept in the National DNA Index System, or NDIS. At this level, an analyst can try to match a DNA profile from a local crime scene sample (also known as a forensic unknown) with an offender's profile from across the nation to solve cases that span states. Analysts use CODIS to search DNA profiles obtained from crime scene evidence against DNA profiles from other crime scenes and from convicted offenders and arrestees. CODIS can generate investigative leads in cases when a match is obtained. For example, if the DNA profile from a crime scene matches a sample taken from another crime scene, the cases may be linked in what is called a forensic hit. If the crime scene sample matches a convicted offender or arrestee sample, the result is called an offender hit. Hits give investigating officers valuable information that helps them focus their investigation. CODIS identifies autosomal genetic markers at 13 STR loci, plus Amelogenin (AMEL) to determine sex. The term "CODIS STR loci" as used herein refers to the thirteen core STR loci designated by the FBI's "Combined DNA Index System." The thirteen core STR loci are TH01, TPDX, CSF1PO, vWA, FGA, D3S1358, D5S818, D7S820, D13S317, D18S539, D8S1179, D18S51, and D21S11. (See, e.g. Vallone et al. For SCi Intl Genetics 3, page 42, 2008; and Butler, Forensic DNA Typing, Academic Press (2001), at page 63.) Use of the CODIS is well known in the art. The 13 loci listed above that are used in the CODIS have been well characterized. See, for example, U.S. Pat. No. 8,562,918. This patent is incorporated by reference herein in its entirety.

Accordingly, in a method of genotyping a sample that includes a nucleic acid as described herein, the method can include comparing the DNA profile obtained to at least one other DNA profile in at least one DNA database using CODIS software. In this embodiment, the at least one DNA database is typically the National DNA Index System, and optionally, a state DNA database. The plurality of genetic markers are typically alleles, and the plurality of STR loci can include one or more CODIS STR loci (i.e., D3S1358, THO1, D21S11, D18S51, D5S818, D13S317, D7S820, D16S539, CSF1PO, vWA, D8S1179, TPDX and FGA). Some embodiments of genotyping a sample include generating a profile of the DNA in the sample, comparing the generated profile with profiles of DNA stored in a database, and upon determining that the generated profile matches one of the stored profiles, identifying the source from which the stored profile was obtained. In forensics, a DNA profile may include a DNA "fingerprint" of multiple, polymorphic genomic loci within a given nucleic acid template, which can then be used in some embodiments to identify the individual (or information about the individual or blood relatives of the individual) from which the nucleic acid template was obtained.

The typical process for typing the CODIS markers is to first isolate DNA from the biologic sample collected and then amplify this sample with primers specific for human DNA in order to provide sufficient material and to avoid amplification of microbial or other possible contaminating non-human DNA. However, using the films, apparatuses, kits and methods described herein, sufficient human DNA is present in and obtained from the primary sample such that this preliminary amplification step is unnecessary.

The sample is then amplified by PCR (polymerase chain reaction) using 15 different primer sets to give samples of each relevant locus. The amplicons for a given locus will have a size reflective of the number of repeats encoded in the sample donor. These will then by separated by capillary electrophoresis and the profiles compared to known genotypes. As with all polymorphic human genes, a given individual's sample may have one or two of the possible alleles depending on whether they are homo or heterozygous at that locus.

The PCR amplification of the 15 loci may take place in separate tubes, there may be groups of genes typed in several tubes or, most efficiently, all will be amplified in the same tube. These splitting or lumping schemes depend on the ability to analyze the various mixes of amplified products. Different strategies to give separation for the various loci have been developed. Two common methods to differentiate one locus from another are 1) use different lengths of the flanking sequences to give size separation and 2) use different dye markers coupled to the PCR primers to give different signals from overlapping peaks when the final products are detected. Subsequently, capillary electrophoresis is used, yielding a tabulated result for typing of a known subject. The frequency at which a subject's genotype is found in a particular population (e.g., a Caucasian population) can be determined using known methods. This methodology is described, for example, in Vallone et al. For SCi Intl Genetics 3, page 42, 2008.

In one embodiment of a method of genotyping a sample as described herein, the entire group of CODIS loci is amplified in a single tube and the profile resulting from this is analyzed in a single run on the capillary electrophoresis instrument. Refinements of this process might include elimination of the first amplification step and automated handling of samples throughout the DNA extraction, amplifications and sample loading and software to determine the genotype and convert it to a form that may be stored in the reference bank. The films described herein are designed to capture sufficient sample and to yield a high percentage of the DNA contained within it thus allowing the standard CODIS analysis to be performed directly upon extraction of the DNA.

In addition to the STR analysis in current use, DNA samples may be subject to more complete determinations such as full-length genomic sequences, specific gene sequences, methylation status of DNA sequences, mtDNA analyses. For example, the increasing use of high throughput DNA sequence analyzers can influence the way in which samples are analyzed in the future and will make the quality of the DNA obtained more highly relevant to the information that can be obtained.

Data obtained about the DNA of a subject using the thin films, thin film collection devices, apparatuses, methods and kits described herein may be stored for subsequent retrieval, such as in a DNA database (e.g., the CODIS). Subsequent cross-comparison of DNA profiles may be made with such information. DNA information may be employed for solving unsolved or "cold" cases (e.g., unsolved cases), for solving property crimes, for identifying persons or victims, or for some other purpose. One or more thin films or thin film collection devices or apparatuses as described herein may be provided as part of a forensic analysis kit. Any of the kits herein may include one or more additional components adapted for nucleic acid collection and typing. Such a kit may include, for example, one or more extraction reagents, buffers for storage and reactions of the DNA, PCR primers, etc.

Stability of collected samples (e.g., biological samples) is critical for accurate analysis and profiling. Results obtained from analyses of the collected samples should be comparable irrespective of the time interval between collection and analysis. In some embodiments, analyses are not performed immediately after sample harvest and there are a number of chemical and biological agents and conditions that can affect the integrity of the sample or of the nucleic acid (e.g., DNA) from it. Insulation from atmospheric conditions by storage in temperature and humidity controlled areas is common to preserve sample integrity. Several methods are known to preserve purified DNA from degradation after primary processing of the samples at the analytical laboratories. The carbohydrate trehalose is one of the compounds currently used as a stabilizer for dried DNA during storage. It is most effective when the purified DNA is stored at about of range of −60° C. to −90° C., and preferably about −80° C. or at ambient temperature (e.g., about 18° C. to 25° C.). In one embodiment, trehalose can be mixed with PCL in a thin film to increase the hydrophilicity of the PCL and, at the same time, give greater stability to the DNA in the sample from the moment of collection.

Kits for Collecting and Analyzing Biologic Analytes

A kit for collecting and analyzing at least one biologic analyte includes at least one film (thin film) as described herein, a biologic analyte extraction reagent; packaging; and instructions for use. The biologic analyte extraction reagent can be, for example, a nucleic acid extraction reagent. The packaging can be any suitable material, e.g., a polymer laminate or plastic container. In one embodiment of a kit, the kit includes a plurality of films as described herein. Generally, in such a kit, each film is disposable, and intended for one use only. In such a kit, each film can be individually packaged, and each packaged film can include an identifying label, bar code, and/or RFID tag. In such an embodiment, the identifying label, bar code, and/or RFID tag is typically affixed or connected to the packaging.

In many applications, the collected sample is not analyzed immediately upon acquisition. An identification means to assure that the collector and the sample can be processed without danger of losing the sample information can be attached to or included with a thin film collection device, kit or apparatus as described herein, e.g., affixed or otherwise attached to a package in which a thin film is packaged. The use of bar codes or quick response ("QR") codes (or other identifying indicia) placed on the packaging at the time of manufacture is one example of a means of retention of sample identity, and in such embodiments, the data linking the collector information with the sample is typically secure. A biologic analyte collection and analysis device or kit as described herein can include one or more of: an RFID tag, a bar code, and a label (e.g., two or more of an RFID tag, a bar code, and a label; all of an RFID tag, a bar code, and a label). An RFID tag can be imprinted with information, such as a bar or QR code. This manufacturer-supplied information can include lot and serial number to unambiguously identify the collection device. Sample collection devices, such as in forensic applications, are used to obtain samples of biological materials for subsequent analyses that serve to establish the identity of the sample source by subsequent analytic steps. How a programmable RFID tag can be implemented in forensic specimen collection, for example, is well known in the art. See, for example, U.S. Pat. Nos. 7,978,074 and 8,759,075, both of which are incorporated herein by reference. The sample collection device may be subject to analyses immediately or it may be stored for some period of time prior to analysis. Often multiple samples must be taken (for example at a crime scene). In this instance the samples may not be analyzed for long periods of time because of a backlog in the laboratory, or the need to send samples for tests not available near the scene of collection. Therefore, in such embodiments, it is important that certain identification criteria accompany the sample.

The present kit embodiments can provide a reagent set that yields information on the quantity of DNA obtained at the collection site. This allows collection of additional samples should the amount be found inadequate. In one embodiment, a thin film kit is provided that allows initial steps of the analytic process to begin in the field and to give an indication of the quantity of DNA obtained. Such a kit can include one or more thin films as described herein packaged with DNA extraction reagents in lyophilized form. In this embodiment, a rapid amplification of DNA follows subsequent to extraction. Following the amplification of the extracted DNA, a colorimetric indicator can be used as a signal that there is (or is not) adequate DNA for complete analysis. This colorimetric indicator can be a DNA-indicating dye included in the reagent, or alternatively, on an impregnated paper to which a drop of solution is added.

In one approach, a kit is provided for use in forensic analyses that can perform the initial steps subsequent to sample collection (such as sample preparation and/or analysis) and also to signal a user that sufficient DNA has been obtained to allow complete analysis of the sample.

Those skilled in the relevant art will appreciate that the embodiments described herein can be practiced with any of various communications, data processing, or computer system devices, including: hand-held devices (including personal digital assistants (PDAs)), wearable computers, cellular or mobile phones, multi-processor systems, microprocessor-based or programmable consumer electronics, network PCs, mini-computers, mainframe computers, and the like. Aspects of the invention described herein may be stored or distributed on computer-readable media, including magnetically or optically readable computer discs, hard-wired or preprogrammed chips (e.g., EEPROM semiconductor chips), nanotechnology memory, biological memory, or other data storage media. Computer-implemented instructions, data structures, screen displays, and other data under aspects of the invention described herein may be distributed over the Internet or over other networks (including wireless networks), on a propagated signal on a propagation medium (e.g., an electromagnetic wave(s), a sound wave, etc.) over a period of time, or they may be provided on any analog or digital network (packet switched, circuit switched, or other scheme).

In a particular embodiment of a kit for collecting and analyzing at least one biologic analyte, the kit is used for collecting a nucleic acid from a fingerprint. Such a "fingerprinting kit" typically includes a housing having side walls coupled to a solid support and a lid, and at least one panel or surface consisting of a film as described herein disposed in the interior of the housing. The configuration of the kit can be similar to standard methods of collecting a fingerprint image but substituting thin film of PCL as described herein for the paper used to collect inked images. In one embodiment, a kit may include a means to collect images on paper as well as fingerprints to be used for DNA extraction. Methods of producing and using fingerprinting kits are well known in the art. See, for example, U.S. Pat. Nos. 5,709,746; 5,398,812; and 5,143,551, all of which are incorporated herein by reference.

In some embodiments, the films, compositions, collection devices, kits and methods described herein are used for collection of low-level (i.e., trace) biologic samples, specifically human fingerprints, and to obtain images of the same fingerprints, i.e., collection of fingerprints for both image capture and nucleic acid (e.g., DNA) extraction. Such films include nanometer thin films made using electrospray technology which are hydrophilic and give >75% blood DNA uptake and release and which also gives touch DNA results. In such embodiments, both physical fingerprint images and DNA resident in a fingerprint are collected. As used herein, the term "latent fingerprints" means any chance or accidental impression left by friction ridge skin on a surface, regardless of whether it is visible or invisible at the time of deposition. Prints taken directly are termed exemplar or known prints, i.e., fingerprints deliberately collected from a subject, whether for purposes of enrollment in a system or when under arrest for a suspected criminal offense. During criminal arrests, a set of exemplar prints will normally include one print taken from each finger that has been rolled from one edge of the nail to the other, plain (or slap) impressions of each of the four fingers of each hand, and plain impressions of each thumb. Exemplar prints can be collected using Live Scan or by using ink on paper cards.

In a typical embodiment of collection, a thin transparent film as described herein, which when used to capture fingerprints, yields usable amounts of DNA. The films, compositions, collection devices, kits and methods can be used to collect biological samples including fingerprints from various surfaces as well as from subjects directly. Surfaces from which the fingerprints can be collected include any object handled, touched or receiving bodily fluids, deliberately or accidentally, from an individual such that material is deposited that can be used to identify the individual. A door, wall, floor, furniture item, glass, dish, cigarette, firearm or other weapons are commonly scanned surfaces for forensics investigations although almost any object or area may qualify. The films and collection devices are assembled into kits for collection of physical prints suitable for digital collections and extraction of DNA of sufficient quantity and quality to be used for subject identification.

Figure 3:
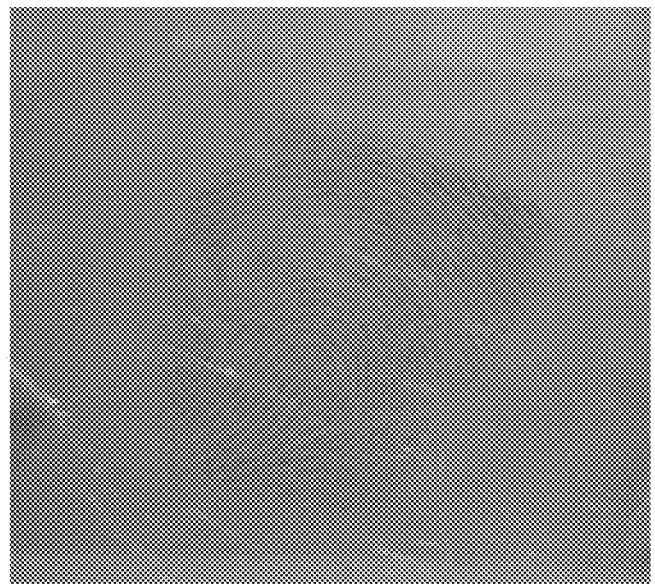
FIG. 3 is a photograph of a fingerprint on a thin film as described herein.
Figure 4:
FIG. 4 is a photograph of a stamp pad used to obtain fingerprints (fingerprint visualization material).

The thin films described herein are many times more efficient in terms of DNA yield from acquired samples than existing devices. Such a thin film is typically approximately 0.03 mm in thickness and weighs about 15 mg. Typically, the amount of DNA obtained from a fingerprint is sufficient to support analyses that may allow generation of DNA profiles suitable for upload to and searching in the CODIS system for subject identification. The films, compositions, collection devices, kits and methods described herein combine the proven superior ability of the PCL-containing thin films to capture useable DNA amounts and to provide a medium for the visualization and digitization of the same fingerprint with materials currently in use for visualization of latent prints. A visualized fingerprint is shown in FIG. 3, and FIG. 4 shows a stamp pad used to obtain fingerprints (fingerprint visualization material). Additional examples of a fingerprint visualization material include inks and dyes and also materials such as powders or other materials that may be deposited on an object to detect latent fingerprints.

Methods of Producing Thin Films

Because of its versatile nature, PCL-based chemistry allows for molding soluble, hydrophilic PCL (referred to in this section as "Diomat™ material") into various different swab conformations for forensic sampling as well as buccal swabs. Likewise, Diomat™ can be applied into thick sheets through standard methods of pouring, spraying, or aliquotting. Additionally, Diomat™ lends itself to more sophisticated technologies such as Electrospray or Electrospinning to form thin films ranging in thicknesses down to several microns (very thin). The same post molding or film-making downstream processes serve to make the various iterations of Diomat™ a superior technology for capture and release of biological materials.

In one method of producing a thin film as described herein, the method includes the steps of: solubilizing PCL in a solvent resulting in a solution; applying the solution to a mold, tray or sheet using an electrospray instrument; freezing the solution; lyophilizing the electrosprayed solution to remove solvent resulting in a film; subjecting the film to treatment with a base having a pH greater than 8 and a neutralizing agent under conditions that result in soluble and hydrophilic PCL; and drying the film. The method can further include the step of sterilizing the film such that it is free of nucleic acids. A film of any suitable size may be produced by this method. In one embodiment, the method is used to produce a film approximately 1.5 inches by 1.5 inches (approximately 38.1 millimeters by 38.1 millimeters), a size particularly useful for finger print collection. The method can further include the step of attaching the film to a carrier, and/or packaging the film. The method can further include spraying the film onto a metallic mesh, plastic, plastic mesh, paper, fiber, cotton or other such device to hold the PCL in place and assist in downstream processing.

The method can further include the step of attaching the film to a carrier, and/or packaging the film. In one embodiment, the method includes applying, attaching or adhering a backing to the resultant film.

In another method of producing a thin film as described herein, the method includes the steps of: solubilizing PCL in a solvent resulting in a solution; applying the solution to a mold, tray or sheet and freezing the solution; lyophilizing the solution to remove solvent resulting in a film; subjecting the film to treatment with a base having a pH greater than 8 and a neutralizing agent under conditions that result in soluble and hydrophilic PCL; and drying the film. The method can further include the step of sterilizing the film such that it is free of nucleic acids. As with the method above, this method can be used to produce a film approximately 1.5 inches by 1.5 inches (approximately 38.1 millimeters by 38.1 millimeters), and can further include the step of attaching the film to a carrier, and/or packaging the film. See FIG. 1 for a flow chart of one embodiment of a method for producing thin films as described herein. A thin film made by this embodiment is shown in FIG. 2.

A thin film as described herein can be manufactured from a variety of chemical solid/solvent combinations. In one form, PCL is solubilized in glacial acetic acid for further rendering into a variety of material forms (e.g. solid objects, swabs, films, etc.) and subsequent shapes and sizes that can be customized for different preferred applications. In one method of thin film synthesis, a Profector Spray Base Electrospray instrument (Model PLS K0003-20, Profector Life Sciences, Dublin, Ireland) was used to prepare films using PCL as follows.

Instruments settings included a voltage of between 0.002 and 20.00 volts with a preferred voltage of around 8.0 volts and a pressure of between 0.002 and 20 mbar with a preferred pressure of around 0.3 mbar. The solution used for the spray consists of a 0.05% to a 6% PCL in acetic acid, with a preferred concentration of 2% PCL. Other solvents for PCL are possible with a requirement that they are inert to stainless steel 316 and are not harmful for human contact (not carcinogenic, not toxic), and preferably have a freezing point between approximately 21° C. and −80° C.

X-Y Axis control on the Profector Spray Base Electrospray of between 0 and 100 for both the X and the Y axis with a preferred range of 30 to 70 for both the X and the Y axis, e.g., holding the X-axis at 30 and stepping the Y-axis from 30 to 70 at a step size of about 0.01 mm to about 0.3 mm (e.g., 0.01 mm) and a velocity of about 0.01 mm/second to about 0.3 mm/second (e.g., 0.1 mm/second) then keeping Y-axis at 70 changing X-axis to 40 and stepping down on Y-Axis from 70 to 30 at a step size of about 0.01 mm to about 0.3 mm (e.g., 0.01 mm) and a velocity of about 0.01 mm/second to about 0.3 mm/second (e.g., 0.1 mm/second) and continuing in an S shaped fashion until film is complete. Initial set-up work must include visualization of the Taylor Cone using the laser and the camera. Switching between the camera mode and the X-Y axis mode is carried out on the computer screen during application.

Operator and observers must use eye protection such as Blue-Green safety glasses with a 650 nm protection to shield from the laser beam, in addition black construction paper or other material is used to prevent reflection of the beam from the plastic. An optional precaution is to coat the stainless steel target plate to prevent sticking of the polymer after application. This coating used for the plate may be canola oil or other lubricating or sealant substances. In absence of such treatment the polymer sticks to the stainless steel but is readily removed when the base treatment occurs.

Time of spray is between 0.001 and 120 minutes with a preferred time of 30 minutes for our small 4 inch diameter plates. After application of the solution to the plate, the material is stored in the −20° C. freezer until lyophilization apparatus is ready. Current lyophilization program includes the following steps in Table 1:

| Hold vs. Ramp | Temperature | Time - minutes | Pressure |
| --- | --- | --- | --- |
| Hold | −20° C. | 120 | 760 |
| Hold | −40° C. | 120 | 760 |
| Hold | −40° C. | 60 | 300 mtorr |
| Hold | −40° C. | 60 | 200 mtorr |
| Hold | −30° C. | 60 | 100 mtorr |
| Hold | −20° C. | 60 | 100 mtorr |
| Hold | −10° C. | 60 | 100 mtorr |
| Hold | 0° C. | 240 | 100 mtorr |
| Hold | 10° C. | 120 | 100 mtorr |
| Hold | 28° C. | 240 | 100 mtorr |

This is one of many possible programs that may work to freeze dry the material and remove solvent. Successful experiments have involved multiple variations in time and pressure made to the above.

After vacuum release, these films are further downstream processed with 1.5 M NaOH treatment for two hours at 22° C. or for 1.5 M NaOH treatment for 18 hours at 24° C. These times, temperatures, and concentrations can be varied. Optimally, a plastic holder of some fashion is placed on the films during the base treatment to prevent curling up of the film. Then, the films are washed with distilled water at 22° C. for 4 to 8 washes until pH 7 is reached.

Then the films are dried in the incubator with a plastic holder on top to prevent curling. This is at 22° C. for 18 to 24 hours.

At this point the films are ready for processing including measurement of water pick up, DNA blood yields and testing for various forensics and diagnostics applications.

The Electrospray process described above gives extremely thin translucent films. Alternatively, films that are thicker and that are also hydrophilic can be obtained without the Spraybase by making a solution of PCL in a solvent, pouring it onto stainless steel, freezing, lyophilizing, base treating, washing, and drying as per the protocol above.

Also possible is the usage of clips or hanging such as in photographic films to stretch out or hold the polymer so that it does not fold over, shrink, or clump as these tend to do. In one embodiment, the film may be sandwiched between wire mesh pieces to prevent curling and allow washing and/or drying.

Results obtained thus far indicate that the films are hydrophilic and can(on a weight basis) take up water at the same level as other Diomat™ devices. Typically these films weigh 10 to 22 mgs. This ability to acquire water is a selection criterion for all new devices. The thin films prepared by several different automated or manual methods have been used to acquire human blood or saliva samples and are then subjected to the extraction and analyses used for other Diomat™-acquired samples. In some embodiments, a film as described herein is approximately 10 to 600 microns. In one example of such an embodiment, a film as described herein has a thickness of approximately 10 to 30 microns.

Solutions used in the production of thin films comprising soluble, hydrophilic PCL can be sterilized using filtration where sterility is maintained by handling the thin film(s) and packaging of the thin film(s) in a clean room environment. Alternatively, a thin film as described herein can be sterilized using UV or gamma irradiation of the finished packaged product. This procedure can also increase wettability and hydrophilicity of the thin film.

PCL for use in the devices, kits and methods described herein can be mixed with several chemicals during manufacture to give varying properties and a desired amount of hydrophilicity. For example, $Ca(Cl)_2$ can be added during a solubilization step of the PCL. As another example, PCL can also be treated with a solution of $Ca(OH)_2$ or NaOH. Both methods can be used to increase the hydrophilicity of the PCL. It is noted though that soluble, hydrophilic PCL can be coupled to and/or copolymerized with a variety of other materials in addition to PCL in various proportions and combinations to yield a thin film with the desired absorbency and solubility. For example, the soluble, hydrophilic PCL can include alginate, silk or other natural fibers.

Any suitable solvent(s) can be used for making a thin film as described herein. The following is a set of preferred criteria for solvents to be used in making thin films:
1. Solvents that PCL is soluble in.
2. Solvents that are impermeable to stainless steel 316.
3. Solvents with a MP of +60 C. to −60 C. (with a lower limit of −90 C.).
4. Solvents that are not carcinogenic, not toxic, and have a reasonable flash point, approximately above 20 C.
5. Solvents that generally include acids, ketones, esters, oils, and natural products or some combination thereof. For instance, a 6% PCL solution in glacial acetic acid also containing a 10% canola oil solution is effective for producing thin films. In another instance, a 6% solution of PCL in 2-hexanone, or a 6% PCL in cyclohexanone, or a 6% PCL in 1,2-dichloroethane, were all effective for producing thin films.
6. Solvents that are a 1,1,0 or a 0,0,0 on the NFPA 704 hazard emergency response rating range. The NFPA 704: Standard System for the Identification of the Hazards of Materials for Emergency Response is a standard maintained by the U.S.-based National Fire Protection Association. First "tentatively adopted as a guide" in 1960, and revised several times since then, it defines the colloquial "fire diamond" used by emergency personnel to quickly and easily identify the risks posed by hazardous materials.

This helps determine what, if any, special equipment should be used, procedures followed, or precautions taken during the initial stages of an emergency response."

Small films (~5 cm diameter) have been manufactured using both manual application and electrospray application of PCL dissolved in acetic acid onto a stainless steel, glass or plastic mold as described above. Such films can be made to a variety of specifications, such as thickness and opacity, and retain their ability to act as bio-absorbants that produce quality downstream DNA yield and sequence data. A preferred conformation of film has been produced using electrospray technology on a stainless steel template that allows making extremely thin films which are then lyophilized.

One method for making larger area films involves using a fixed-position nozzle over a movable X, Y, Z axis platform. Another method would involve a movable nozzle, with X, Y, Z axis control, over a fixed platform. A preferred design would involve using an electrospray apparatus and nozzle in each of these conformations. In each case, the mold or template that receives the spray is formed from high grade stainless steel that allows good heat transfer during downstream lyophilization.

Films of varying shape and dimension can be produced by establishing an electrospray nozzle on a movable platform with X, Y, and Z axis movement controlled, spraying down onto a stainless steel template. The size of the template is only limited by the shelf-size of the lyophilizer into which the applied PCL film is processed. For larger templates, which take longer to apply the sprayed PCL, it may be necessary to freeze or cool the template during the application process to prevent evaporation of the early sprayed material. This cooling could be accomplished by a variety of methods, including, but not limited to, a Pelletier device under the template. Typically, the trays are placed into a −20° C. freezer or onto pre-cooled shelves of the lyophilizer, also at −20° C.

EXAMPLES

The present invention is further illustrated by the following specific examples. The examples are provided for illustration only and should not be construed as limiting the scope of the invention in any way.

Example 1

Production of Thin Films

A 2% PCL solution in Acetic Acid is made up by adding 0.8042 g PCL and 40 mL AcOH, heating and stiffing in an 80° C. oil bath with a 60° C. internal temperature for two hours followed by 22° C. room temperature for one hour. Four Films were made using the Profector SprayBase. All of the films were made at 10+/−1 volts and 0.4 to 0.6 mbarr pressure. Times varied from 5 to 20 minutes per 4 inch diameter circular 316 stainless steel tray. These films were incubated at −20 C until all films were ready, about one hour, then lyophilized according to program. These were released from the lyophilizer and incubated at room temperature (21° C.) in 1.5 M NaOH, 20 mL each film, for four hours, then washed three times with 20 mL of room temperature water, pH=7, and dried. Films are between 0.08 mm and 0.2 mm in thickness and a 16.0 mg sample film picks up 41 mg of 0.1% Thymol Blue solution.

Example 2

Additional Thin Film Production Methodology

A 2% PCL solution in Acetic Acid is made up by adding 0.8190 g PCL and 40 mL AcOH, heating and stiffing in an 80° C. oil bath with an 60° C. internal temperature for two hours followed by 22° C. room temperature for one hour. Four Films were made using the Profector SprayBase. All of the films were made at 10+/−1 volts and 0.4 to 0.6 mbarr pressure. Times varied from 5 to 20 minutes per 4 inch diameter circular 316 stainless steel tray. These films were incubated at −20° C. until all films were ready, about one hour, then lyophilized according to program. These were released from the lyophilizer and incubated at room temperature (21° C.) in 1.5 M NaOH, 20 mL each film, for two hours, then washed three times with 20 mL of room temperature water, pH=7, and dried. Films are between 0.08 mm and 0.2 mm in thickness and a 16.5 mg sample picks up 45 mg of 0.1% Thymol Blue solution.

Example 3

Additional Thin Film Production Methodology

A 2% PCL solution in Acetic Acid is made up by adding 0.4136 g PCL and 20 mL AcOH, heating and stiffing in an 80° C. oil bath with an 60° C. internal temperature for two hours followed by 22° C. room temperature for one hour. Four Films were made using the Profector SprayBase. All of the films were made at 7 to 10 volts and 0.1 to 0.3 mbarr pressure. Times varied from 6 to 8 minutes per 4 inch diameter circular 316 stainless steel tray. These films were incubated at −20° C. until all films were ready, about one hour, then lyophilized according to program. These were released from the lyophilizer and incubated at room temperature (21° C.) in 1.5 M NaOH, 20 mL each film, for two hours, then washed three times with 20 mL of room temperature water, pH=7, and dried. Films are between 0.03 mm and 0.09 mm in thickness and a 10.8 mg sample picks up 41 mg of 0.1% Thymol Blue solution, and a 3.9 mg sample picks up a 34.9 mg of 0.1% Thymol Blue Solution.

Example 4

Recovery of Blood DNA from Thin Film

Samples of thin film were weighed and their thickness determined with a caliper. Each thin film sample was used to pick up 1 microliter of blood from a glass slide and then allowed to air dry for at least two hours. The samples were then subjected to DNA extraction process and the yields compared to that of a blood sample allowed to dry in an extraction tube for the same period

TABLE 2

Recovery of DNA from Film Samples Picking up 1 microliter human Blood

| Film Sample | Weight of film (mg) | Thickness (Caliper) (mm) | DNA Uptake and Release[a] |
|---|---|---|---|
| 1 | 15.5 | 0.03 | 70% |
| 2 | 16.1 | 0.03 | 68% |
| 3 | 16.2 | 0.03 | 42% |
| 4 | 15.3 | 0.10 | 61% |

TABLE 2-continued

Recovery of DNA from Film Samples Picking up 1 microliter human Blood

| Film Sample | Weight of film (mg) | Thickness (Caliper) (mm) | DNA Uptake and Release$^a$ |
|---|---|---|---|
| 5 | 10.7 | 0.03 | 81% |
| 6 | 12.0 | 0.03 | 61% |
| 7 | 13.3 | 0.06 | 52% |

Recoveries of DNA ranged from 7 to 12 nanograms of DNA for the thin film samples compared to 15 ng for the dried blood sample in the extraction tube. The percentage numbers shown in the table represent the amount of DNA recovery compared to the control sample.

Example 5

Recovery of DNA from Film Samples Picking up Human Blood and Fingerprints

Samples of Diomat™ Thin film weighing approximately 15 mg were exposed to 1 ul human blood diluted 1/10 or, alternatively were impressed with fingerprints. All samples were dried and DNA extracted from them and quantified. Results shown below indicate that samples used to pick up blood samples averaged 50% of DNA recovered from blood added to tube directly. The fingerprint samples yielded about 1.3 ng of DNA which is sufficient to give results in standard analytic methods.

TABLE 3

| Diomics ID | ng DNA | avg ng | % blood std |
|---|---|---|---|
| 140916-1 | 14.3 | 15.6 | 54.74% |
|  | 17.3 |  |  |
|  | 15.3 |  |  |
| 140916-2 | 13.3 | 13.5 | 49.27% |
|  | 13.0 |  |  |
|  | 14.3 |  |  |
| 140802-1 | 1.4 | 1.4 | NA |
|  | 1.2 |  |  |
|  | 1.5 |  |  |
| 140806-1 | 1.9 | 1.3 | NA |
|  | 0.6 |  |  |
| Blood in tube | 26.2 | 28.5 | 100.00% |
|  | 28.1 |  |  |
|  | 31.1 |  |  |
| Reagent Blank | 0.0 |  |  |

Samples 140916-1 and −2 are thin films exposed to 1 ul human blood
Samples 140802-1 and 140806-1 are thin films exposed to human fingerprints Example 6

DNA and Latent Fingerprint Collection from Same Sample

The films, compositions, collection devices, kits and methods described herein can be used for collection of low-level (i.e., trace) biologic samples, specifically human fingerprints, and to obtain images of the same fingerprints, e.g., collection of fingerprints for both image capture and DNA extraction (FIG. 3). Such films include nanometer thin films made using electrospray technology which are hydrophilic and give >75% blood DNA uptake and release and which also gives touch DNA results. These films were shown to capture DNA from fingerprints and give level 2 detail fingerprints.

Collection of samples for evidentiary use is a major requirement in law enforcement. Classically the use of fingerprints has served to identify individuals touching items at crime scenes and the use of digital imagery has allowed large databases to be compiled and accessed in a rapid and efficient manner. Since the 1980's the use of DNA samples obtained by extraction of biologic materials has enhanced law enforcement's ability to identify persons leaving biologic evidence at a crime scene or handling materials relevant to criminal activity. An obviously ideal situation would involve the ability to capture both types of information from samples obtained at crime scenes in the most effective manners and subsequently exploit existing databases of latent print and fingerprint images and DNA profiles for comparison purposes.

Films, compositions, collection devices, kits and methods for collection of biologic samples and analysis of DNA obtained from them can involve collection of both physical fingerprint images (FIG. 3) and DNA resident in a fingerprint. In a typical embodiment of collection, a thin transparent film as described herein, which when used to capture fingerprints (FIG. 3), yields usable amounts of DNA. The films, compositions, collection devices, kits and methods can be used to collect biological samples including fingerprints from various surfaces as well as from subjects directly. The films and collection devices are assembled into kits for collection of physical prints suitable for digital collections and extraction of DNA of sufficient quantity and quality to be used for subject identification.

The thin films described herein are many times more efficient in terms of DNA yield from acquired samples than existing devices. Such a thin film is typically approximately 0.03 mm in thickness and weighs about 15 mg. In tests where fingerprints were placed on thin film fragments and then extracted for DNA, the yields were in all cases between 0.9 and 1.4 ng of DNA. These results are unexpected in that this quantity range is sufficient to support analyses that may allow generation of DNA profiles suitable for upload to and searching in the CODIS system, for example, for subject identification. The films, compositions, collection devices, kits and methods described herein combine the proven superior ability of the PCL-containing thin films to capture useable DNA amounts and to provide a medium for the visualization (FIGS. 3 and 4) and digitization of the same fingerprint with materials currently in use for visualization of latent prints.

Other Embodiments

Any improvement may be made in part or all of the compositions, devices, kits and method steps. All references, including publications, patent applications, and patents, cited herein are hereby incorporated by reference. The use of any and all examples, or exemplary language (e.g., "such as") provided herein, is intended to illuminate the invention and does not pose a limitation on the scope of the invention unless otherwise claimed. Any statement herein as to the nature or benefits of the invention or of the preferred embodiments is not intended to be limiting, and the appended claims should not be deemed to be limited by such statements. More generally, no language in the specification should be construed as indicating any non-claimed element as being essential to the practice of the invention. This invention includes all modifications and equivalents of the subject matter recited in the claims appended hereto as permitted by applicable law. For example, although in a typical thin film embodiment no attachment of the thin film to a carrier is required, in some embodiments, a thin film of soluble and hydrophilic PCL may be coupled to a carrier. Moreover, any combination of the above-described elements in all possible variations thereof is encompassed by the invention unless otherwise indicated herein or otherwise clearly contraindicated by context.

What is claimed is:

1. A transparent or semi-transparent hydrophilic thin film consisting essentially of polycaprolactone and a backing applied or adhered to one side of the film, the polycaprolactone having been treated with a base having a pH greater than 8 and a neutralizing agent having a thickness in the range of about 0.01 mm to about 0.6 mm that provides greater than 75% blood DNA uptake and release, wherein at least a portion of the hydrophilic film solubilizes when exposed to at least one reagent for extraction of biological analytes, and wherein the hydrophilic film has been sterilized such that it is free of nucleic acids, wherein the transparent or semi-transparent hydrophilic film is configured for collection of DNA from latent fingerprints and to obtain images of the latent fingerprints, wherein the at least one biologic analyte extraction reagent is unaffected by fingerprint visualization materials, and wherein the fingerprint visualization materials comprise ink for detecting fingerprints.

2. The transparent or semi-transparent hydrophilic thin film of claim 1, wherein the transparent or semi-transparent hydrophilic thin film is packaged within packaging, and the packaging comprises at least one of: an identifying label imprinted with information, a radio-frequency identification tag, and a bar code.

3. The transparent or semi-transparent hydrophilic thin film of claim 1, wherein the transparent or semi-transparent hydrophilic thin film is produced by electrospray.

4. The transparent or semi-transparent hydrophilic thin film of claim 1, wherein the at least one reagent for extraction of biological analytes is not phenol-chloroform.

5. A transparent or semi-transparent hydrophilic thin film consisting essentially of polycaprolactone, and a backing applied or adhered to one side of the film, the film produced by:
    solubilizing polycaprolactone in a solvent resulting in a solution;
    applying the solution to a mold;
    freezing the solution;
    removing solvent from the solution resulting in a film;
    subjecting the film to treatment with a base having a pH greater than 8 and a neutralizing agent under conditions that result in soluble and hydrophilic polycaprolactone; and
    drying the film, wherein the film provides greater than 75% blood DNA uptake and release and has a thickness in the range of about 0.01 mm to about 0.6 mm, wherein at least a portion of the film solubilizes when exposed to at least one reagent for extraction of biological analytes, wherein the hydrophilic film has been sterilized such that it is free of nucleic acids, wherein the transparent or semi-transparent hydrophilic film is configured for collection of DNA from latent fingerprints and to obtain images of the latent fingerprints, wherein the at least one biologic analyte extraction reagent is unaffected by fingerprint visualization materials, and wherein the fingerprint visualization materials comprise ink for detecting fingerprints.

6. The transparent or semi-transparent hydrophilic thin film produced by the process of claim 5, wherein the solution is applied to the mold using an electrospray instrument.

7. A kit for identifying a trace sample's donor, the kit comprising:
    at least one transparent or semi-transparent hydrophilic thin film according to claim 1;
    at least one biologic analyte extraction reagent excluding phenol-chloroform;
    ink for detecting fingerprints, wherein the transparent or semi-transparent hydrophilic film is used for collection of DNA from latent fingerprints and to obtain images of the latent fingerprints, wherein the at least one biologic analyte extraction reagent is unaffected by fingerprint visualization materials;
    packaging; and
    instructions for use.

8. The kit of claim 7, wherein the kit comprises a plurality of the transparent or semi-transparent hydrophilic films, and each transparent or semi-transparent hydrophilic thin film is individually packaged.

9. The kit of claim 8, wherein each package comprises at least one of: an identifying label imprinted with information, a radio frequency identification tag and a bar code.

10. The kit of claim 7, further comprising a housing having side walls coupled to a solid support and a lid, and at least one panel consisting of the transparent or semi-transparent hydrophilic thin film of claim 1 disposed in the interior of the housing.

11. The kit of claim 7, further comprising a silica membrane spin column.

* * * * *